US008252590B2

(12) United States Patent
Jorquera Nieto et al.

(10) Patent No.: US 8,252,590 B2
(45) Date of Patent: Aug. 28, 2012

(54) MAMMALIAN CELL CULTURE MEDIA WHICH COMPRISE SUPERNATANT FROM COHN FRACTIONATION STAGES AND USE THEREOF

(75) Inventors: Juan Ignacio Jorquera Nieto, Parets del Valles (ES); Montserrat Costa Rierola, Parets del Valles (ES); José María Diez Cervantes, Parets del Valles (ES)

(73) Assignee: Grifols, S.A., Barcelona (ES)

(*) Notice: Subject to any disclaimer, the term of this patent is extended or adjusted under 35 U.S.C. 154(b) by 0 days.

(21) Appl. No.: 12/829,449

(22) Filed: Jul. 2, 2010

(65) Prior Publication Data

US 2011/0027891 A1    Feb. 3, 2011

(30) Foreign Application Priority Data

Jul. 28, 2009    (ES) .................................. 200930526

(51) Int. Cl.
    C12N 5/02    (2006.01)
(52) U.S. Cl. .................. 435/404; 435/407; 435/408
(58) Field of Classification Search .................. 435/404, 435/407, 408
    See application file for complete search history.

(56) References Cited

FOREIGN PATENT DOCUMENTS

| CA | 1 177 424 | | 11/1984 |
|---|---|---|---|
| EP | 0 143 648 A2 | | 6/1985 |
| EP | 143648 A2 | * | 6/1985 |
| EP | 0 201 800 A2 | | 11/1986 |
| EP | 0 264 748 A2 | | 4/1988 |
| EP | 0 440 509 A2 | | 8/1991 |
| EP | 1 820 852 A1 | | 8/2007 |
| GB | 2 166 756 | | 5/1986 |
| GB | 2166756 A | * | 5/1986 |
| WO | WO 94/18310 | | 8/1994 |
| WO | WO 9418310 A1 | * | 8/1994 |
| WO | WO 2004/055174 | | 7/2004 |

OTHER PUBLICATIONS

Partial European Search Report issued Aug. 18, 2010 in corresponding EP 10 38 0080.
Extended Partial Search Report issued Nov. 17, 2010 in corresponding EP 10 38 0080.
Healy et al "Selective Nucleolar Uptake of OK-Acid Glycoprotein by Mammalian Cells in Tissue Culture" Biochimica et Biophysica Acta (1967) Vol. 148, No. 2, pp. 556-558.
Jo E-C et al. "microcarrier Culture of Bowes Melanoma Cells in Serum-Free Medium with Human Plasma Fraction IV-4-Plus-V" *Biotechnology and Bioengineering* vol. 38, No. 3, pp. 247-253.
Evans et al. "Advances in Tissue Culture at the National Cancer Institute in the Unites States of America" in *Tissue Culture*, edited by C.V. Ramakrishanan, W. Junk, The Hague (1965) pp. 145-167.
Barnes et al., "Methods for Growth of Cultured Cells in Serum-Free Medium" Analytical Biochemistry, (1980), vol. 102, pp. 255-270.
Cohn et al., "Preparation and Properties of Serum and Plasma Proteins. IV. A System for the Separation into Fractions of the Protein and Lipoprotein Components of Biological Tissues and Fluids" J. Am. Chem. Soc., 1946, vol. 68, No. 3, pp. 459-475.
Curling, "Albumin Purification by Ion Exchange Chromatography" Methods of Plasma Protein Fractionation, Academic Press, 1980, pp. 77-91.
Eagle, "The Specific amino Acid Requirements of a Mammalian Cell (Strain L) in Tissue Culture" *Amino Acid Needs of Mammalian Cells* J. Biol. Chem., (1954), vol. 214, pp. 839-852 (www.jbc.org).
Eagle, "Nutrition Needs of Mammalian Cells in Tissue Culture" Science, (1955), vol. 122, No. 3168, pp. 501-504.
Evans et al., "Studies of Nutrient Media for Tissue Cells in Vitro. I A Protein-Free Chemically Defined Medium for Cultivation of Strain L Cells" Cancer Res., (1956), vol. 16, No. 1, pp. 77-86.
Evans et al., "Studies of Nutrient Media for Tissue Cells in Vitro. II. An Improved Protein-free Chemically Defined Medium for Long-Term Cultivation of Strain L-929 Cells" Cancer Res., (1956), vol. 16, No. 1, pp. 87-94.
Friedli et al., "Removal of Ethanol and Salt from Albumin by Gel Filtration" Methods of Plasma Protein Fractionation, Academic Press, 1980, pp. 203-210.
Ham, "Clonal Growth of Mammalian Cells in a Chemically Defined, Synthetic Medium" Microbiology :R.G. Ham *Proc. N.A.S.* (1965), vol. 53, pp. 288-293.
Ham et al., "Development of Improved Media and Culture Conditions for Clonal Growth of Normal Diploid Cells" in Vitro, (1978), vol. 14, No. 1, pp. 11-22.
Ham R. G., "An Improved Nutrient Solution for Diploid Chinese Hamster and Human Cell Lines" Experimental Cell Research, (1963), vol. 29, Issue 3, pp. 515-526.
Kistler et al., "Large Scale Production of Human Plasma Fractions" *Vox Sang.*, (1962), vol. 7, pp. 414-424.
Kistler et al., "Ethanol Precipitation" Methods of Plasma Protein Fractionation, Academic Press, 1980, pp. 3-15.
Macleod, "The Use of Plasma Protein Fractions as Medium Supplements for Animal Cell Culture" *Advances in Biochemical Engineering Biotechnology*, (1988), vol. 37, pp. 41-56.
Morgan et al., "Nutrition of animal cells in tissue culture. I Initial studies on a synthetic medium". Proc. Soc. Exp. Biol. Med., (1950), vol. 73, No. 1, pp. 1-8.
Morton et al., "Nutrition of Animal Cells in Tissue Culture. II. Use of Tweens in Synthetic Feeding Mixtures" Proc. Soc. Exp. Biol. Med., (1950), vol. 74, No. 1, pp. 22-26.

* cited by examiner

*Primary Examiner* — Michele K Joike
*Assistant Examiner* — Antonio Galisteo Gonzalez
(74) *Attorney, Agent, or Firm* — Buchanan Ingersoll & Rooney

(57) ABSTRACT

The present invention relates to mammalian cell culture media which comprise supernatant from some of the fractions of human plasma fractionation according to the Cohn method, more specifically, the supernatant of fractions I and II+III. When said supernatant is added as a culture medium supplement it provides various nutrients and factors for the effective maintenance and/or proliferation of the cultured mammalian cells. In addition, the present invention relates to the preparation process and use of said medium in the culture of mammalian cells.

9 Claims, No Drawings

MAMMALIAN CELL CULTURE MEDIA WHICH COMPRISE SUPERNATANT FROM COHN FRACTIONATION STAGES AND USE THEREOF

FIELD OF THE INVENTION

The present invention relates to a supplement for use in mammalian cell culture media. Said supplement is obtained from defibrinated human plasma (substantially free from fibrinogen and fibrin) and, when it is added as a supplement to culture media it provides the different nutrients and factors for the satisfactory maintenance and/or proliferation of cultured cells.

BACKGROUND

Cell cultures are used in the biotechnology industry principally to produce recombinant proteins and monoclonal antibodies. Recently however, a technology has been developed to culture different types of core cells for use in cell therapy, in combination or not with gene therapy.

To successfully culture and maintain the different cell lines, a medium is required that imitates the conditions of the internal medium in which these cells are found in vivo. Generally, the culture medium consists of a basal medium which provides the pH, nutrients and salts and to which a series of supplements may be added to ensure cell proliferation. One of the most widely used supplements is animal blood serum. As a result of the animal origin of the serum there may be serious restrictions for its use to obtain products for use in humans, because residues of animal origin are recognised as foreign antigens and may cause adverse reactions in the recipients. Furthermore, animal sera have the drawback of lacking a defined composition, as there is a great variability between manufacturers because different animal breeds are used. In addition, because of the method by which they are obtained, there is great variability between batches, which means that wide variations may occur in growth capacity and in the production of a particular culture.

The main difficulty in establishing cell lines is obtaining suitable nutritive media which are capable of replacing the natural medium, such as embryo extracts, protein hydrolysates or sera. A first group of media, such as the Eagle basal medium (MEM) (Eagle, H. (1955) "The specific aminoacid requirements of mammalian cells (strain L) in tissue culture". J. Biol. Chem. 214: 839) and the more complex 199 medium of Morgan et al. (Morgan, J. G., Morton, J. H. and Parker, R. C. (1950) "Nutrition of animal cells in tissue culture. I Initial studies on a synthetic medium". Proc. Soc. Exp. Biol. Med. 73: 1) were defined media but they require a serum supplement of between 5% and 20%.

To eliminate the contribution of undefined complex media more complex media have been formulated such as NCTC 109 (Evans, V. J., Bryant, J. C., Fioramonti, M. C., McQuilkin, W. T., Sanford, K. K., and Earle, W. R. (1956) "Studies of nutrient media for tissue C cells in vitro. I A protein-free chemically defined medium for cultivation of strain L cells" Cancer Res. 16: 77), 135 (Evans, V. J. and Briant, J. C. (1965) "Advances in tissue culture at the National Cancer Institute in the United States of America" in "Tissue culture", edited by C. V. Ramakrishnan, W. Junk, The Hague, pp. 145-167), Ham F10 and F12 (Ham, R. G. (1963). "An improved nutrient solution for diploid Chinese hamster and human cell lines". Exp. Cell Res. 29: 515, Ham, R. G. (1965) "Clonal growth of mammalian cells in a chemically defined synthetic medium" Proc. Natl. Sci. USA 53: 288), MCDB series (Ham, R. G. and McKeehan, W. L. (1978) "Development of improved media and culture conditions for clonal growth of normal diploid cells" In vitro 14: 11-22) and hormone-supplemented Sato media (Barnes, D. and Sato, G. (1980) "Methods for growth of cultured cells in serum-free medium" Anal. Biochem. 102: 255-270).

The recommended approach in order to establish a defined medium is to begin with a rich medium, for example Ham F12, supplemented with a high concentration of serum (20%) and test supplements for reducing the quantity of serum until it can be reduced or eliminated.

After years of investigation into the composition of media, they are still selected empirically.

The principal media used and their applications are:

Eagle Basal Medium (EBM). This is a basic medium with only essential aminoacids. It always requires supplementation with 10% foetal calf serum. It is used for growing mouse fibroblasts and HeLa cells.

Eagle's Minimum Essential Medium (MEM). This is the most commonly used medium, which contains more aminoacids in a higher concentration than EBM. It is used for almost any type of culture and requires the addition of serum (10%).

R.P.M.I. 1640. This is a medium designed for growing lymphoblasts and leukaemia cell lines in suspension. With suitable supplements, it has a wide range of applications.

Dulbecco Modified Eagle Medium (DMEM). It contains four times the concentration of aminoacids and vitamins as EBM. It is used for selecting hybridomas supplemented with HAT (hypoxanthine-aminopterin-thymidine) or HT (hypoxanthine-thymidine).

Iscove modified DMEM (IMDM). This is a very complete medium with a formulation that includes bovine albumin, transferrin and selenite, among other elements. It is very useful in the culture of lymphocytes in serum-free medium. It is also used for other cell types, but in this case requires low concentrations of serum.

McCoy 5a medium. Designed for growing diploid cell lines of both rats and humans.

Leibovitz L-15 medium. Used for the culture of viruses.

Ham F-10 medium. It is used for growing human cell lines and must be supplemented with proteins and hormones. It contains metals such as Fe, Cu and Zn. It is used for amniotic cell culture.

Ham F-12 medium. It is used for growing cell lines with protein supplements. Combined with IMDM it can be used as a serum-free medium.

Medium 199. It is used very widely for undifferentiated cell culture and for studying chromosome disorders.

All culture media consist of the following elements:
1. Balanced saline solutions (BSS).
2. Aminoacids.
3. Vitamins.
4. Other organic supplements with a low molecular weight (nucleosides, Krebs cycle intermediates, pyruvate, lipids).
5. Hormones and growth factors (serum).
6. Contaminant growth inhibitors (antibiotics and antifungals).

In undefined media, the serum usually provides hormones and growth factors. The types of serum used are calf serum (CF), foetal calf serum (FCS), horse serum (HS) and human serum (HuS). The most widely used is calf serum, while foetal calf serum is used in more demanding lines and human serum is used in human lines.

The use of serum is problematic as despite the composition of the serum being known in part, there are a great many components present in variable quantities which may significantly influence the culture. In addition, the serum varies from batch to batch, due to the variability of the technique for obtaining blood, the method of obtaining the serum (blood coagulation) and the conditions for separating the serum, as well as the difference between the various sources of serum. Moreover, each change of serum batch requires a series of tedious and costly checks. Further, if the products of the culture medium have to be purified, the presence of variable components in the serum makes these processes significantly more difficult.

Some serum factors, such as the platelet-derived growth factor (PDGF), stimulate the proliferation of fibroblasts, which may be a problem in establishing specialised primary cultures, particularly if there is a wide variation in their content.

On the whole, the inclusion of serum in culture media is a significant drawback to standardising experimental protocols and cell production. Great efforts are therefore being made to establish media with a defined composition for cell growth. As well as the reproducibility sought, this allows selective media to be established in which the cell type required can grow. The disadvantage of these media is that in many cases cell growth is lower and cell lines remain viable for fewer generations.

Various attempts have been made to produce supplements for cell culture media which avoid the problems posed by the sera used at present. Among these, various fractions from human plasma have been tested and there are significant contradictions in the prior art as to the usefulness of the different human plasma fractions.

In general, different human plasma fractions originating from plasma fractionation using the Cohn method have been tested (Cohn E. J. et al; J Am Chem Soc, 1946) and variations thereof (Kistler and Friedli, Nischmann; in Curling, J M ed, Methods of plasma fractionation, Academic Press 1980), all these tests being directed towards the use of the different precipitates obtained in the fractionation, particularly the II+III, III, IV ($IV_1$ or $IV_4$) and V fractions, or their equivalents in different variants of the fractionation method.

The initial aim in separating the above-mentioned fractions (precipitate) is to obtain a precipitate enriched with a particular protein as a starting point for the purification of said protein, for example γ-globulins and α and β-globulins in the case of the II+III or III fractions; α-globulins and transferrin in the IV fraction and albumin in the V fraction. These fractions therefore usually have a single type of protein, other proteins being present as impurities, usually in far smaller quantities. The use of these fractions in cell cultures involves adding to the culture medium a major protein type and a variety of proteins which accompany it as impurities, among which must be present those required by the cells in the culture medium if the use of said material is to be successful. Until now this has been an obvious but inefficient way of supplementing cell culture media. This is certainly the cause of the disparity in the results obtained, as small variations in the fractionation method will not significantly affect the recovery of the major protein, but may introduce great variability in the recovery of the various accompanying proteins. For example, the II+III fraction using the Cohn method is obtained at an ethanol concentration of between 20% and 25% at −5° C. and a pH of 6.9. Using the Nitschmann method, starting with equivalent material, it is precipitated at an ethanol concentration of 19% at −5° C. and a pH of 5.8. With this variation in the pH, fractions are obtained with different characteristics, particularly in the content of γ-globulins and other accompanying proteins.

Furthermore, the use of supernatants, compared with the use of precipitated fractions, has additional advantages, including that of maintaining a high albumin concentration in the medium and, above all, avoiding the loss of components (for example hormones, cytokines, lipids, etc.) which are important for cell growth and which may not be present in the precipitates or may lose their functionality (be inactivated) in the presence of alcohol concentrations of more than 20%, such as those used to precipitate the II+III fraction in certain conditions (25%) or the $IV_1$+$IV_4$ and V fractions (40% ethanol).

Document EP0143648 (Macleod) describes the use of the II+III, III, $IV_1$ and $IV_4$ fractions as supplements for culture media instead of animal serum. It also states that neither the II fraction nor the V fraction is useful for this application. In all cases, this document refers exclusively to fractions precipitated in the Cohn fractionation or its variants. In addition, the document discloses a method for obtaining material suitable for supplementing culture media from the above-mentioned fractions. This method consists basically of suspending the precipitate in water and homogenising said precipitate. Next, the pH is adjusted to achieve better protein dissolution and produce the physiological conditions for cell growth. Further, this method also considers the elimination of the γ-globulin present by precipitation with polyethylene glycol and the separation of material of low molecular weight by molecular-exclusion chromatography. The effectiveness of the material prepared in this way is therefore very dependent on the specific preparation method.

Another document by Macleod (Advances in Biochemical Engineering/Biotechnology, Vol. 37; 1988) indicates that the II, III and IV fractions have little or no effect on cell growth, possibly due to the presence of growth inhibitors and focuses attention on the $IV_4$ fraction as the ideal material to supplement culture media.

EP 0 440 509 (Macleod) describes a supplement for cell culture media based on the Cohn's IV fraction or II+III fraction, and the process for obtaining it. Using the process described, a product is obtained which is substantially free from immunoglobulins, is virus-inactivated and stable. The immunoglobulin is separated by precipitation with polyethylene glycol and viruses are inactivated by pasteurization, in the presence of sorbitol as a stabiliser. This process is particularly applicable to the IV ($IV_1$ or $IV_4$) fraction.

Document EP 0264748 (Antoniades) describes the supernatant of the Cohn V fraction as a supplement for cell culture media instead of animal serum. According to this document, the advantage of this material is that there is no cost and it can be heated to 60° C. for 20 hours.

The supernatant of the V fraction is the final waste material from the Cohn fractionation and therefore its use clearly has no economic cost to detract from the benefits of said fractionation. This material has a high ethanol content (40%), which is highly toxic and which this document does not state must be eliminated. Furthermore, for the treatment described at 60° C. the protein present would have to be stabilised, but this detail is also omitted from the document, making the invention difficult to produce as described. Nor should the denaturing effect of ethanol at so high a concentration as in this case be underestimated.

WO 94/18310 (Mankarious) describes a method for producing a supplement for cell culture media from the Cohn $IV_4$ fraction. This method looks at the suspension and subsequent clarification of the $IV_4$ fraction and also the inactivation or elimination of viruses by pasteurization and/or filtration.

Patent GB 2 166 756 A describes a method for the culture of spleen cells for the production of interferon. This method is based on an RPMI culture medium which is supplemented by a serum fraction obtained from serum or plasma from which the fibrinogen has been eliminated and which is characterised in that the prealbumin and gammaglobulins have been removed (page 1, lines 30-34). In a preferred embodiment, this fraction is purified by precipitation with alcohol between 10% and 20%, at a pH of 5.85 (page 1, lines 37-38). In a particular embodiment (obtaining the EPF fraction), the supernatant used as a culture medium is obtained at an ethanol concentration of 19% and a pH of 5.85 (page 2, lines 44-45). The supernatant obtained is dialysed in order to eliminate the ethanol, and is subsequently lyophilised to preserve it. Optionally, it is lyophilised with no prior dialysis, and consequently the ethanol is also eliminated. According to the inventors, by using a culture medium (RPMI) supplemented with said fraction, excellent interferon production is obtained. In the alcohol precipitation of the plasma, the process conditions (ethanol concentration, pH, ion strength of the medium, temperature and protein concentration) must be carefully set to maintain particular proteins in solution and insolubilize others so that they are precipitated and can thus be separated. Variations in one or more of said conditions will produce significant differences in the product obtained, the ethanol concentration and pH being the factors determining the composition of the precipitate and supernatant obtained.

Other attempts have been made to supplement cell culture media using serum or serum fractions of human origin, instead of foetal calf serum, as shown in documents WO 2004/055174, EP 1820852 or CA 1177424. The serum obtained from complete blood or from plasma cannot be compared with a specifically defined and characterised plasma fraction and has the drawback of lacking reproducibility between batches. In addition, none of these documents succeeds in defining and characterising the exact composition of the material used. Therefore the majority of the problems associated with the use of serum of animal origin continue to arise.

Kwok et al. disclosed the use of plasma from pregnant women instead of foetal calf serum for the culture of specific cell types, attributing its effect to the presence of unknown factors. He also postulates a synergic effect of human albumin in this type of culture. It is clear to a person skilled in the art that by using plasma from pregnant women the presence is sought of cell growth factors comparable to those of foetal serum, but the homogeneity of this material is not comparable to plasma mixtures from thousands of donors, as described below.

As described hereabove, numerous attempts have been made to replace animal serum as a cell culture medium supplement. Some of these attempts were made from human plasma fractions, particularly fractions using the Cohn method. Despite which, at present animal serum continues to be widely used as a supplement for mammalian cell culture media and attempts to replace it with a derivative of human plasma have failed.

From all of the above, it can be deduced that in the prior art no material of human origin is available which could be used to supplement cell culture media and which is also safe as regards the transmission of pathogenic agents, can be obtained on an industrial scale at an acceptable cost and profit, has adequate uniformity between batches and is of pharmaceutical grade quality.

DESCRIPTION OF THE INVENTION

The inventors have carried out research aimed at replacing serum of animal origin as a supplement for culture media with human plasma fractions and they have found, surprisingly, that starting from a Cohn fractionation supernatant, specifically the supernatant of the II+III fraction or the supernatant of the I fraction, it is possible to supplement cell culture media and obtain excellent results as regards cell growth. The use of this material solves the above-mentioned problems as it is of human origin, is obtained industrially using good manufacturing practices (GMPs), with acceptable costs and profits, shows adequate uniformity and reproducibility between batches and is of pharmaceutical grade quality. Moreover, the material can be treated by methods that avoid the transmission of pathogens.

The procedure for preparing these derivatives is described below.

First, human plasma from healthy donors is obtained to which an anticoagulant solution is added containing, in a preferred use of the invention, only sodium citrate in sufficient quantity to ensure that the plasma does not coagulate. The addition of substances (for example carbohydrates such as glucose) to improve preservation of the blood cells is not essential, because the plasma used in the invention is substantially cell-free, as it has been possible to obtain it by plasmapheresis in the presence of anticoagulant, instead of by complete blood donation.

The quantities of anticoagulant and other standards that the process of obtaining, storing and handling human plasma must meet are described in publicly available international standards affecting the human plasma fractionation industry, such as, for example the United States of America's Code of Federal Regulations, the directives and standards of the United States' Food and Drug Administration (FDA) and the European Medicines Evaluation Agency (EMEA), as well as the directives and standards of the International Conference of Harmonization (ICH) and international pharmacopoeias, such as the European, Japanese or United States pharmacopoeias, and also standards known as current Good Manufacturing Practices (cGMP). In the rest of this document all these standards will be referred to as "the set of standards affecting human plasma fractionation for pharmaceutical purposes". This set of standards also applies to the stages of the invention which are described below.

Once human plasma has been obtained, it is frozen, stored and transported in accordance with the set of standards affecting human plasma fractionation for pharmaceutical purposes and, in a preferred use of the invention, specifically according to the requirements of the European Pharmacopoeia's Monograph 0853. Each plasma unit (donation) is analysed to rule out the presence of viral infection markers in the donors, who have previously been subjected to questionnaires and physical examinations in accordance with the above-mentioned standards. In a preferred application of the invention, the plasma of a possible donor is not used until the donor has undergone the evaluation process twice in under six months, at which time the donor becomes "qualified donor".

In a preferred application of the invention, samples obtained from each donation are analysed to rule out the presence of markers for infections such as, for example, the human immunodeficiency virus (HIV), the hepatitis B and C viruses (HBV and HCV) and other viruses pathogenic to man. Part of the invention is the controlled storage of plasma donations for a period of not less than 60 days, preferably not less than 90 days, which would allow previous donations to be withdrawn if a previously healthy donor shows signs of infection by pathogenic agents or other health risk factors after the donation. In a preferred application of the invention, the analyses of samples from each donation are repeated one or more times after preparing pilot mixtures (minipools or pilot pools) from a variable number of donations which may fluctuate, for example, between 10 and 10,000, preferably between 90 and 2000 and more preferably between 100 and 1000. Methods of amplifying the genetic material of the viruses may be used for these repeated analyses, such as, for example, the polymerase chain reaction (PCR) or other methods generically included among those known for nucleic acid testing (NAT).

Once all the analyses and the controlled storage period (inventory hold) are complete, and after ruling out units found unsuitable by the analyses, the plasma may be used in later stages of the invention.

The next stage consists of thawing donations numbering no less than 100 units, preferably above 1000 units and more preferably above 4000 units. In a preferred application of the invention, thawing may take place at a temperature of between 0° C. and 4° C. The donations are mixed during the thawing process to produce a plasma mixture (plasma pool). Optionally, a precipitated material may be separated, as it is unstable due to the thawing process. It is usually described as cryoprecipitate and is rich in von Willebrand factor (FVW), VIII factor (FVIII), fibrinogen (FBN), fibronectin (FNC) and other proteins.

Next, in a preferred use of the invention, 96% pharmaceutical grade ethanol is added to the plasma up to a concentration of approximately 8% (volume/volume). To ensure that the proteins are not denatured due to the exothermic process of dissolving ethanol in the plasma, it is added in a controlled volume. Simultaneously, and with the same object, the temperature of the plasma pool is gradually reduced to approximately −2° C. The presence of ethanol ensures that the plasma does not freeze. In these conditions, a protein fraction is precipitated which is very rich in fibrinogen and includes the majority of the proteins present in the cryoprecipitate if said cryoprecipitate, in an application of the invention, has not been separated prior to the addition of alcohol. This fraction is known generically as Cohn fraction I (Fr-I), because it is obtained by a process basically corresponding to that described by Edwin J. Cohn (Cohn E. J. et al; J Am Chem Soc, 1946). When the precipitate obtained at this stage is separated, the supernatant fraction is found to be substantially fibrinogen-free, and therefore free from any interference that fibrinogen could cause in the cell cultures, it being suitable for the object of the invention as a supplement for cell culture media, once the added alcohol has been eliminated, because of its cell toxicity.

In a preferred application of the invention, after having separated any or none of the two precipitates described earlier (cryoprecipitate and Fr-I), 96% pharmaceutical grade ethanol is added to the existing mixture to a concentration of between 20% and 25% (volume/volume). To avoid protein denaturing due to the exothermic process of dissolving ethanol in the plasma, the addition is carried out at a controlled volume. Simultaneously, and with the same object, the temperature of the plasma pool is gradually reduced to approximately −5° C. The presence of ethanol ensures that the plasma does not freeze. In these conditions a protein fraction is precipitated which is very rich in the proteins described previously as present in the cryoprecipitate and in the Fr-I (if it has not already been separated, as described earlier) and is also very rich in immunoglobulins, principally IgG and IgM. This fraction is known generically as I+II+III fraction (Fr-I+II+III), if the Cohn Fr-I fraction has not previously been separated, or II+III fraction (Fr-II+III) if the Cohn Fr-I has previously been separated. When the precipitate obtained at this stage is separated, the supernatant fraction is found to be substantially free from fibrinogen and immunoglobulins and therefore free from interference that could be caused by these proteins in the cell cultures, it being suitable for the object of the invention as a supplement for cell culture media, once the added alcohol has been eliminated because of its cell toxicity.

During the stages described controls are applied to the process for producing plasma derived materials to ensure that the processes take place in accordance with the required specifications regarding protein concentration, pH, microorganism count, etc.

These supernatants are obtained by a process which corresponds basically to that described by Edwin J. Cohn, although there may be differences in composition, due both to changes in the scale of production (number of donations and volume of the plasma pools) and to variations between the process according to the invention and the process applied at that time.

These supernatants, obtained directly from the industrial fractionation of human plasma (based on the Cohn method), apart from the elimination of the ethanol they contain (approximately 8% in the I fraction supernatant and approximately 20%-25% in the II+III fraction supernatant), do not require subsequent purification treatments.

The ethanol contained in these supernatants may be eliminated by any of the known methods in the prior art. Preferably it is performed by dialysis or diafiltration or directly by lyophilisation, evaporation or desiccation (for example spray drying), such methods being easy to industrialize.

A valid preparation method to obtain a completely stable product consists of starting with any of the supernatants described and, optionally, diluting them appropriately with injection water, physiological saline solution or buffer, at a pH of 7-8 and a temperature of between 2-8° C. The solution is clarified through cellulose plates or deep plates which are inert with regard to protein adsorption, and finally it is clarified to a pore size of approximately 0.5 microns. The product then undergoes diafiltration, using membranes of approximately 10 kDa nominal molecular cut-off, against two or more volumes of injection water, physiological saline solution or buffer, at a preferred pH of approximately 7. Preferably, the number of diafiltration exchange volumes is approximately 5.

The diafiltered solution is clarified by absolute filtration with a filter gradient of 0.2 to 0.1 micron pore size. Next the product may be nanofiltered through a pore size of approximately 35 nm and 20 nm, preferably at a temperature of 2-8° C. and a transmembrane pressure of less than or equal to 1 bar. The load applied is preferably about 70 litres/m$^2$ of area for the filter with the smaller pore size.

The product obtained may be concentrated by ultrafiltration to the same total protein concentration value as the starting material (supernatant), or more concentrated if preferred.

In either case, the material obtained is measured into glass phials or bottles and stored preferably at −30° C. or at a lower temperature until it is used. In a step prior to measuring the supernatant into phials, a sterilizing filtration may be carried out through a pore size of between 0.1 and 0.2 microns.

The frozen product may also be lyophilised or subjected to other treatments to provide a dried product. The product may then be subjected to gamma radiation and can be kept in the dried state preferably at 2 to 8° C. until used.

If diafiltration is not performed on the starting material (S/Fr-I or S/Fr-II+III, or equivalent) and elimination of the alcohol directly by lyophilisation is chosen, it is measured into glass vials or bottles. Prior to measuring the supernatant into phials, a sterilizing filtration process may be performed through a pore size of between 0.1 and 0.2 microns. The measured material is frozen preferably at a temperature of less than or equal to −30° C., and subjected to lyophilisation and gamma radiation using known techniques.

Optionally, the material may be treated with methods for eliminating/inactivating pathogenic agents. Preferably the material, either frozen or lyophilised is irradiated, with gamma radiation at between 15 and 35 kilo-grays, the optimum between composition stability and elimination of viruses being obtained with 25 kilo-grays.

The lyophilised product may be stored for a long period of time, preferably at between 2-8° C.

As regards cell proliferation, the supernatant of Fr-II+III is kept stable (proliferation percentages equal to (100±20)% or greater than FCS) for at least 168 days in lyophilised form, kept in a freezer (2-8° C.).

This material, reconstituted in Ham F12 culture medium is stable for at least 113 days at a temperature of less than or equal to −18° C. (cell proliferation percentages equal to or greater than time zero).

The stability of Ham F12 culture medium, supplemented with 50% S/Fr-II+III is four days in a freezer.

A preferred way of preserving the material until it is used is as a lyophilisate in its final packaging. In this way, it can be measured into doses directly and the ethanol can be eliminated in the actual lyophilisation process.

These supernatants are added to conventional serum-free culture media containing inorganic salts, aminoacids and vitamins among other necessary components for cell growth, such as Ham F12 medium or Dulbecco modified medium (DMEM), for example.

The resulting medium may be used to culture a wide variety of mammalian cells. Conventional techniques and culture conditions known to a person skilled in the art are used for this purpose.

The lyophilised supernatant may be reconstituted in basal culture medium, for example Ham F12 medium or Dulbecco modified minimum essential medium (DMEM), in distilled water or deionised and apyrogenic water, or in saline solutions or buffers common in cell culture.

The supernatant reconstituted in a culture medium may be used to supplement the basic culture medium by adding between 2% and 50% (v/v) of reconstituted supernatant, for example: 2 ml of fraction I supernatant or fraction II+III supernatant reconstituted in a medium with 98 ml of basic medium (2%). Another example would be to add 50 ml of fraction I supernatant or fraction II+III supernatant reconstituted in a medium with 50 ml of basal medium (50%).

It is recommended that the supernatant reconstituted in water, saline solutions or buffers suitable for cell culture be added to the basal culture medium at between 2% and 20% (v/v) for example 20 ml of reconstituted supernatant in 80 ml of medium (20%). If concentrations of 50% (v/v) are required, the reconstituted supernatant would have to be added to double concentrated base medium (2×) for example adding 50 ml of fraction I supernatant or fraction II+III supernatant in water to 50 ml of 2× basic medium.

The supplemented culture medium may be used for the usual culture techniques and this supplemented medium may be used directly or filtered beforehand through 0.22 μm.

Preserved frozen material (supernatant) must be thawed prior to being added to the basic medium. Once thawed it is recommended that it be added to the basic culture medium at between 2% and 20% (v/v) for example 20 ml of fraction II+III supernatant reconstituted in 80 ml of medium (20%). If concentrations of 50% (v/v) are required, when supplementing the medium fraction I or fraction II+III supernatant would have to be added double concentrated (2×) for example adding 50 ml of fraction II+III supernatant to 50 ml of 2× basic medium.

The supplemented culture medium may be used for the usual culture techniques and the supplemented medium may be used directly or after being filtered through 0.22 μm.

EXAMPLE 1

Preparation of the Supernatant of Fractions I and II+III

Individual plasma donations produced by plasmapheresis are mixed and thawed, thawing being carried out in a reactor at a controlled temperature of between 0° C. and 4° C. Ultimately, 3783 kg of plasma are obtained.

To separate the cryoprecipitate, the plasma is centrifuged at between 9000 and 12000×g, while maintaining the centrifugation temperature at between 0° C. and 4° C.

To separate the fraction I, the protein concentration of the cryoprecipitate supernatant (C/S), which should be approximately 5%, is checked. If it is higher, it is diluted with injection water. The pH is also adjusted to approximately 7.

Beginning with the C/S, ethanol is added to a concentration of 8% (volume/volume). The speed at which the ethanol is added must be slow (less than or equal to 2 kg/min) with moderate agitation to avoid denaturation. During the addition of ethanol the temperature of the supernatant is gradually reduced in the precipitation reactor until it reaches a final temperature of −2° C. The final pH must be approximately 7.

After about two hours of reaction, centrifugation is carried out to separate the fraction I. This centrifugation takes place at between 9000 and 12000×g. The supernatant obtained (S/Fr-I) is kept at a temperature of between 0° C. and −4° C.

At this point, or in the C/S, the prothrombin complex may optionally be extracted by ion exchange chromatography (Curling, J M ed; Methods of plasma fractionation, Academic Press 1980).

To separate the fraction II+III, the pH of the S/Fr-I is adjusted to approximately 7 and ethanol is then added to take it to approximately 20% (volume/volume). The speed at which the ethanol is added must be slow (less than or equal to 2 kg/min) and with moderate agitation to avoid denaturation. During the addition of the ethanol, the temperature of the supernatant is gradually reduced in the precipitation reactor to a final temperature of approximately −5° C. The final pH should be about 7.

In this example, after approximately six hours of reaction time the fraction II+III is separated.

At this point (supernatant of the fraction II+III), or in the C/S, or in the S/FrI the antithrombin may optionally be extracted by heparin affinity chromatography (Fernandez J. et al., Sangre 41 (supl. 3) 42 (1996).

EXAMPLE 2

Dose Measurement and Lyophilisation

A supernatant of the fraction II+III obtained according to Example 1 is diluted with injection water to a pH of 7-8 and a temperature of between 2° C. and 8° C. until an ethanol concentration of 8% is achieved. The solution is clarified through cellulose plates of up to 0.5 microns pore size. Next the product is subjected optionally to diafiltration to eliminate the ethanol, using polysulphone membranes of 10 kDa nominal molecular cut-off, in the presence of injection water, at a pH of 7. The number of exchange volumes during diafiltration is 5.

The solution is clarified by absolute filtration with a filter gradient of 0.2 microns to 0.1 microns pore size. Next, the product is optionally nanofiltered through a pore size of 35 nm and 20 nm, with cupra-ammonium cellulose filters at a temperature of between 2° C. and 8° C. and a transmembrane pressure of less than 1 bar, at most until the filters are blocked.

The product is concentrated by ultrafiltration to the same total protein concentration value as the starting material and, following sterilizing filtration through a pore size of 0.2 microns, is measured into glass phials and stored at −30° C. until used.

The frozen product may be lyophilised to provide a dried product which is subjected to gamma radiation and may be kept at between 2° C. and 8° C. until used.

EXAMPLE 3

The majority composition of different batches of material obtained according to example 2 (lyophilised supernatants reconstituted in $H_2O$), compared with that of foetal calf serum is shown in the tables below:

| BATCH | Foetal calf serum n = 3 (x ± DT) | Fraction II + III supernatant n = 3 (x ± DT) | Fraction I supernatant n = (1-4)* |
|---|---|---|---|
| Total protein (BIORAD) (mg/ml) | 32.13 ± 2.07 | 30.81 ± 2.29 | 38.39 |
| Electrophoresis (Albumin %) | 46.86 ± 1.22 | 76.27 ± 1.73 | 62.35 |
| Electrophoresis (Alphaglobulin 1%) | 44.93 ± 1.49 | 4.64 ± 0.18 | 3.41 |
| Electrophoresis (Alphaglobulin 2%) | | 9.28 ± 1.48 | 10.24 |
| Electrophoresis (Betaglobulin %) | 6.13 ± 0.32 | 7.74 ± 0.43 | 11.33 |
| Electrophoresis (Gammaglobulins %) | 1.02 ± 0.16 | 1.63 ± 0.30 | 12.37 |
| Electrophoresis (rest %) | 0-0.26 | 0.08-0.63 | 0.31 |
| Albumin(g/l) | ND | 23.8 ± 2.1 | 27.500 |
| α-ANTITRYPSIN(g/l) | ND | 0.915 ± 0.05 | 1.270 ± 0.09 |
| Alpha-1-acid glycoprotein (g/l) | ND | 0.574 ± 0.06 | 0.760 ± 0.05 |
| Apo-AI (g/L) | ND | 0.354 ± 0.07 | 0.804 ± 0.07 |
| Haptoglobin(g/l) | ND | 0.826 ± 0.05 | 1.173 |
| α2-macroglobulin (g/l) | ND | 0.296 ± 0.04 | 1.529 ± 0.16 |
| ATIII (g/l) | ND | 0.200 ± 0.01 | 0.228 ± 0.02 |
| Apo-AII (g/L) | ND | 0.195 ± 0.02 | 0.233 ± 0.01 |
| Ceruloplasmin(g/l) | ND | 0.147 ± 0.02 | 0.269 ± 0.03 |
| Transferrin(g/l) | ND | 1.615 ± 0.11 | 1.883 |
| Hemopexin(g/l) | ND | 0.442 ± 0.01 | 0.662 ± 0.03 |
| Plasminogen (g/l) | ND | <0.0228 | 0.092 |
| Apo-B (g/L) | ND | <0.0428 | 0.570 ± 0.03 |
| Fibrinogen (g/l) | ND | <0.0329 | 0.285 |
| IgG (g/l) | ND | 0.347 ± 0.03 | 6.370 |
| IgA (g/l) | ND | 0.496 ± 0.03 | 1.807 |
| IgM (g/l) | ND | 0.043-0.1105 | 1.125 ± 0.37 |
| Osmolality (mOsm/kg) | 302.00 ± 12.29 | 234.67 ± 35.30 | 632.5 |
| Turbidity (NTU) | 21.52 ± 2.20 | 158-281 | 2753 |
| pH (1%) | 7.39 ± 0.03 | 8.42 ± 0.14 | 9.44 |
| Bicarbonate (mmol/L) | 13.00 ± 1.73 | 2-6 | 18 ± 9 |
| Chlorides (mmol/l) | 106.00 ± 1.00 | 71.80 ± 3.12 | 182 |
| Potassium (mmol/l) | 10.67 ± 0.58 | 2.87 ± 0.23 | 6 |
| Sodium (mmol/l) | 137.33 ± 3.21 | 130.33 ± 4.93 | 252 |
| Calcium (mg/L) | 139.90 ± 8.03 | 53.07 ± 6.45 | 65.70 ± 0.87 |
| Phosphorus (mg/dL) | 9.37 ± 1.08 | 2.17 ± 0.21 | 2.97 ± 0.06 |
| Zinc (μg/L) | 3162.67 ± 523.64 | 611.50 ± 24.75 | 1318 |
| Lead (μg/L) | <5 | <5 | <5 |

*= 3 of the batches are analysed before being lyophilised.
ND = Not determined

| | BATCH | | |
|---|---|---|---|
| | Foetal calf serum n = 3 (x ± DT) | Fraction II + III supernatant n = 3 (x ± DT) | Fraction I supernatant n = (1-4)* (x ± DT) |
| Molecular distribution (%) | | | |
| Polymers and aggregates | 7.26-16.83 | 2.85-8.12 | 9.57 |
| Intermediate forms | 9.84 ± 3.08 | 10.18 ± 1.48 | 31.30 |
| Monomer | 78.34 ± 1.83 | 84.20 ± 0.87 | 59.12 |
| PM < monomer | 0-0.17 | 0-1.47 | 0.00 |
| GLUCOSE (mg/dL) | 46-77 | 63.33 ± 6.66 | 82.67 ± 2.08 |
| UREA (mg/dL) | 34.67 ± 1.53 | 18.33 ± 3.06 | 23.75 ± 0.50 |

-continued

|  | BATCH | | |
|---|---|---|---|
|  | Foetal calf serum n = 3 (x ± DT) | Fraction II + III supernatant n = 3 (x ± DT) | Fraction I supernatant n = (1-4)* (x ± DT) |
| URIC ACID (mg/dL) | 1.83 ± 0.15 | 3.17 ± 0.35 | 4.30 ± 0.08 |
| BUN-UREA NITROGEN (mg/dL) | 16.29 ± 0.72 | 8.62 ± 1.44 | 11.16 ± 0.23 |
| CREATININE (mg/dL) | 2.95 ± 0.40 | 0.52 ± 0.12 | 0.84 ± 0.08 |
| BUN/creatinine ratio | 5.62 ± 1.02 | 16.75 ± 1.40 | 13.16 ± 1.12 |
| TOTAL BILIRUBIN (mg/dL) | 0.20 ± 0.03 | 0.23 ± 0.03 | 0.31 ± 0.03 |
| Alkaline phosphatase (U/g protein) | 0.03-1.14 | 0.78 ± 0.10 | 1.06 ± 0.19 |
| Gamma-glutamyl transpeptidase (GGT) (U/L) | 9.67 ± 0.58 | 14.67 ± 2.08 | 16 |
| Serum Glutamic-Oxaloacetic Transaminase (SGOT) (U/L) | 24.00 ± 3.46 | 9.00 ± 1.73 | 8 |
| Lactate dehydrogenase (LDH) (U/L) | 433.67 ± 38.18 | <50 | <50 |
| BASAL INSULIN (µU/mL) | 76.97 ± 12.45 | <2-2.53 | 12.23 ± 1.78 |
| 17-BETA ESTRADIOL (pg/mL) | 30.77 ± 7.45 | 41.13 ± 6.09 | 46.78 ± 5.07 |
| PROGESTERONE (ng/mL) | <0.20-0.20 | 0.46-0.85 | 0.80 ± 0.13 |
| TOTAL TESTOSTERONE (ng/mL) | 0.14 ± 0.02 | 1.79 ± 0.28 | 2.52 ± 0.14 |
| FREE TESTOSTERONE (pg/mL) | <0.03-0.17 | 3.69 ± 0.49 | 3.98 |
| TOTAL THYROXINE (T4) (µg/dL) | 13.07 ± 0.47 | 4.12 ± 0.34 | 6.51 ± 0.38 |
| FREE T4 (ng/dL) | 3.00->6 | 0.99 ± 0.09 | 1.17 ± 0.10 |
| TRIGLYCERIDES (mg/dL) | 59 ± 6.56 | 18.67 ± 0.58 | 117.25 ± 8.54 |
| CHOLESTEROL (mg/dL) | 34 ± 4.36 | 31 ± 4.58 | 137.50 ± 4.12 |
| HDL-CHOLESTEROL (mg/dL) | 9.67 ± 1.53 | 9.33 ± 2.08 | 6-14 |
| LDL-CHOLESTEROL (mg/dL) | 10-17 | 17.67 ± 3.06 | 105.25 ± 2.22 |
| VLDL-CHOLESTEROL (mg/dL) | 11.67 ± 1.53 | 4 | 23.50 ± 1.73 |
| FREE FATTY ACIDS (mEq/L) | <0.10 | 0.19 ± 0.03 | 0.30 ± 0.1 |
| TOTAL PHOSPHOLIPIDS (mg/dL) | 44.33 ± 4.04 | 57 ± 5.00 | 152.50 ± 38.39 |

*= 3 BATCHES ARE ANALYSED BEFORE BEING LYOPHILISED.

| BATCH | Foetal calf serum n = 3 (x ± DT) | Fraction II + III supernatant n = 3 (x ± DT) | Fraction I supernatant n = (1-4)* (x ± DT) |
|---|---|---|---|
| SATURATED FATTY ACIDS (%) | | | |
| Tetradecanoic (myristic. C14:0) | 0.30-0.90 | 0.50-1.45 | 0.10-0.90 |
| Hexadecanoic (palmitic C16:0) | 25.80 ± 0.66 | 25.67 ± 0.49 | 28.40 ± 3.67 |
| Octadecanoic (stearic C18:0) | 21.03 ± 2.40 | 11.50 ± 0.28 | 9.40 ± 2.09 |
| Eicosanoic (arachidic C20:0) | 0.20-0.40 | 0.20 | 0.20 |
| Docosanoic (behenic C22:0) | 0.23 ± 0.06 | 0.10 | ≦0.10 |
| MONOSATURATED FATTY ACIDS (%) | | | |
| Hexadecenoic (palmitoleic C16:1) | 1.10-2.10 | 1.13 ± 0.06 | 1.83 ± 0.36 |
| Cis-9-octadecenoic (oleic C18:1) | 19.43 ± 3.48 | 16.92 ± 0.26 | 11.90-27.10 |
| Cis-11-octadecenoic (cis-vaccenic C18:1) | 0.20-6.60 | 1.05-2.40 | <0.10-1.20 |
| 11-eicosenoic (gondoic C20:1) | 0.23 ± 0.06 | 0.10 | ≦0.10 |
| POLYUNSATURATED FATTY ACIDS (ω3 ω6) (%) | | | |
| Cis,cis,cis-9,12,15-octadecatrienoic (alpha-linolenic C18:3) | 0.23 ± 0.06 | 0.10-0.30 | 0.20-0.50 |
| Cis-5,8,11,14,17-eicosapentaenoic (EPA C20:5) | 0.30-1.20 | 0.10-0.80 | <0.10-0.50 |
| Cis-4,7,10,13,16,19-decosahexaenoic (DHA C22:6) | 3.93 ± 0.93 | 0.45-1.40 | 0.40-1.2 |
| Cis,cis-9,12-octadecadienoic (linoleic C18:2) | 2.63 ± 0.29 | 26.28 ± 0.59 | 27.23 ± 4.15 |
| Cis,cis,cis-6,9,12-octadecatrienoic (gamma-linolenic C18:3) | 0.23 ± 0.06 | 0.20-0.40 | <0.10-0.40 |
| Cis-11,14-eicosadienoic (C20:2) | 0.23 ± 0.06 | 0.10 | ≦0.10 |
| Dihomo-gamma-linolenic (C20:3) | 2.27 ± 0.31 | 1.70 ± 0.09 | 0.30-1.60 |
| Cis,cis,cis,cis-5,8,11,14-eicosatretraenoic (arachidonic C20:4) | 4.60-7.80 | 8.62 ± 0.62 | 7.00 ± 0.80 |
| All-cis-7,10,13,16,19-docosapentaenoic (C22:5) | 3.83 ± 0.68 | 0.45-0.75 | 0.55 ± 0.07 |

*= 3 BATCHES ARE ANALYSED BEFORE BEING LYOPHILISED.

EXAMPLE 4

Cell Proliferation Test of the CHO Line with Medium Supplemented with Fraction I Supernatant The CHO cell line consists of Chinese hamster ovarian cells which have an epithelial morphology and grow adhesively. The culture used comes from the European Collection of Cell Cultures (ECACC), catalogue no. 85050302.

Fraction I supernatant is reconstituted with Ham F12 culture medium as mentioned above.

Different concentrations (volume/volume) of fraction I are cultured in culture medium (20%; 40%; 60%; 80% and 100%) and in medium supplemented by 20% (v/v) foetal calf serum (FCS) and unsupplemented medium.

A 96-well plate is seeded with 50 µl per well of a suspension of CHO cells at a concentration of between $5\times10^5$ and $1\times10^6$ cells/ml in unsupplemented culture medium.

50 µl per well of the medium to be tested is added to each column of the plate so that the final dilution will give unsupplemented medium, supplemented with 10% FCS and with 10%, 20%, 30%, 40% and 50% of fraction I supernatant.

The 96-well plate is incubated at 37° C. in an atmosphere with 8% $CO_2$ and high relative humidity (cell culture incubator) for 48 hours.

100 µl of unsupplemented medium are added to a column as a comparison sample.

After 48 hours of incubation, 10 µl of WST-1/ECS reagent from the commercially available Millipore cell proliferation assay kit, catalogue no. 2210, is added to each well.

After 2 to 4 hours incubation under the usual culture conditions for the line (37° C.; 8% $CO_2$) a plate is agitated for one minute and the absorbency is measured in a microplate reader at a wavelength of 420-480 nm, the reference wave length reading being greater than 600 nm (plates are usually read in a Tecan SUNRISE reader at a wavelength of 450 nm and a reference wavelength of 620 nm using Magellan software V 6.3 for reading and data analysis to check the apparatus).

Absorbency values higher than the comparison sample plus twice the standard deviation thereof are considered positive for this technique.

In the next step the average value of the comparison sample is subtracted from the rest of the wells in the plate.

The average values of the wells of each column are calculated (once the comparison sample for this technique has been subtracted) matching the average value of each column to the average value for the unsupplemented medium and the medium supplemented with FCS or with different concentrations of fraction I supernatant respectively.

Cells in unsupplemented medium are considered not to proliferate (0%) and therefore the average absorbency value in this column is subtracted from all the average values of all the columns.

The absorbency value of the reference medium (Ham F12 medium supplemented with 10% FCS) is taken as the 100% proliferation value and therefore, once the value of the unsupplemented medium has been subtracted, all the average values from the previous point are divided by this value to obtain the proliferation percentage relative to the reference medium.

With media supplemented by between 20% and 50% fraction I supernatant, as a general rule, the proliferation percentages obtained are similar to the reference medium (medium with 10% foetal calf serum) or very much higher (medium with 50% fraction I supernatant).

The proliferation results are shown below as percentages.

| | CHO cell proliferation (%) in Ham F12 medium supplemented with FCS or S/Fr I | | | | | |
|---|---|---|---|---|---|---|
| S/S | 10% FCS (2.5 mg mg/ml alb) | 10% S/Fr. I (6 mg/ml alb) | 20% S/Fr. I (12 mg/ml alb) | 30% S/Fr. I (17 mg/ml alb) | 40% S/Fr. I (23 mg/ml alb) | 50% S/Fr. I (29 mg/ml alb) |
| 0 | 100 | 70 | 120 | 168 | 206 | 233 |

S/S with no supplement;
FCS: foetal calf serum;
alb: albumin

EXAMPLE 5

Cell Proliferation Test of the CHO Cell Line with Medium Supplemented by Fraction II+III Supernatant The test performed was identical to the previous test, supplementing the media with fraction II+III supernatant instead of fraction I supernatant.

As to the proliferation results, using 20% fraction II+III supernatant to supplement the medium, the results are similar to those obtained with the reference medium (supplemented with 10% FCS) and when media supplemented with 50% fraction II+III supernatant are used, the proliferation results are greater than those obtained with the reference medium.

The proliferation results are shown below as percentages.

| | CHO cell proliferation (%) in Ham F12 medium supplemented with FCS and S/Fr-II + III (n = 4) | | | | |
|---|---|---|---|---|---|
| S/S | 10% FCS (2.5 mg mg/ml alb) | 20% S/Fr II + III (4.8 mg/ml alb) | 30% S/Fr. II + III (7.1 mg/ml alb) | 40% S/Fr. II + III (9.5 mg/ml alb) | 50% S/Fr. II + III (11.9 mg/ml alb) |
| 0 | 100 | 85 | 104 | 123 | 160 |

S/S with no supplement;
FCS: foetal calf serum;
alb: albumin

EXAMPLE 6

Cell Proliferation Test of the CHO Cell Line with Medium Supplemented by Gamma Irradiated Fraction II+III Supernatant The test performed was identical to the previous test supplementing the media with fraction II+III supernatant irradiated with gamma radiation, at doses of 25 and 35 kGy (kilo Grays).

As to the proliferation results, no significant differences are shown to exist between the results obtained with fraction II+III supernatant without irradiation and with irradiation with 25 and 35 kGy.

The proliferation results are shown below as percentages.

| CHO cell proliferation (%) in Ham F12 medium supplemented with FCS, S/Fr-II + III or gamma irradiated S/Fr-II + III | | | | |
|---|---|---|---|---|
| S/S | 10% FCS | 50% S/Fr.II + III [G3] | 50% S/Fr.II + III 25 kGy | 50% S/Fr.II + III 35 kGy |
| 0 | 100 | 155 | 150 | 142 |

S/S with no supplement;
FCS: foetal calf serum;
kGy: kiloGrays

EXAMPLE 7

Cell Proliferation Test of the Vero Cell Line with Medium Supplemented by Gamma Irradiated Fraction II+III Supernatant (25 kGy)

The test performed was identical to the test in Example 1, using as the basic culture medium, Dulbecco modified minimal essential medium (DMEM), and the Vero cell line instead of the CHO line.

The Vero cell line consists of kidney cells of the African green monkey, the morphology of these cells being similar to fibroblasts (fibroblast-like) with an adhesive growth habit. The culture used comes from the European Collection of Cell Cultures (ECACC), catalogue no. 84113001.

The proliferation results obtained show a result very similar to or greater than that obtained with the reference medium above 30% supplementation with gamma-irradiated fraction II+III supernatant. The medium supplemented with 20% gamma irradiated fraction II+III supernatant gives very similar results to the reference medium (basic medium supplemented with 10% FCS).

The proliferation results are shown below as percentages.

EXAMPLE 8

Subculture of the CHO Cell Line with Ham F12 Medium Supplemented by 50% Fraction II+III Supernatant (25 kGy)

A bottle with a CHO cell culture generally close to confluence is used.

The culture medium is decanted.

The cell monolayer is washed using phosphate buffered saline (PBS) at a temperature of between 20° C. and 37° C., using approx 10 ml per 25 $cm^2$ and decanted.

A solution containing trypsin 0.05%/EDTA 0.02% is added (the trypsin may be recombinant or of animal origin) using 2 ml per 25 $cm^2$ of cultured surface. The solution is spread over the entire surface so that it forms a thin film and the excess solution is decanted.

The bottle is kept at a temperature of between 20° C. and 37° C. until the cells separate from the surface.

Ham F12 culture medium supplemented with 50% fraction II+III supernatant (25 kGy) is added at between 5 ml and 15 ml per cultured bottle.

The cells are dissociated by agitating the bottle or pipetting, and the cells counted.

They are dispensed into new culture bottles distributed in a proportion of between 1:3 and 1:10.

The total volume of Ham F12 medium supplemented with 50% fraction II+III supernatant (25 kGy) in the new culture bottles should be 0.2 to 0.3 ml/$cm^2$ of culture surface.

The bottle is incubated in a cell culture incubator at 37° C. with high relative humidity and a $CO_2$ concentration appropriate to the culture medium used (in this case 8%).

The culture medium must be changed every one to three days.

After various passes using the culture medium supplemented with 50% S/Fr-II+III (25 kGy), it was observed that the culture remained viable and had growth capacity.

Viability, population doubling time (PDT) and total number of cells on a 75 $cm^2$ surface were monitored for 16 consecutive passes resulting in an average viability of 92.79%, an average PDT of 73.8 hours and an average total number of cells of 4.34×$10^6$ cells/75 $cm^2$. The results obtained using the reference medium during nine consecutive passes were average viability of 97.81%, average PDT of 27.49 hours and average total number of cells of 1.28×$10^7$ cells/75 $cm^2$.

In a second experiment, the same parameters were monitored in CHO cells cultured using 50%, 20% and 10% S/Fr-II+III during 3 to 7 passes. For cells cultured in medium supplemented with 50% S/Fr-II+III, a PDT of 103.22, viability of 90.21% and 6.14×$10^6$ cells/75 $cm^2$ were obtained. For cells cultured in medium supplemented with 20% S/Fr-II+III, a PDT of 70.45, viability of 94.89% and 7.72×$10^6$ cells/75 $cm^2$ were obtained. For cells cultured in medium supple-

| Vero cell proliferation (%) in DMEM medium supplemented with FCS or gamma irradiated S/Fr-II + III (n = 8) | | | | | | | | |
|---|---|---|---|---|---|---|---|---|
| S/S | 2% FCS (0.5 mg/ml alb) | 5% FCS (1.3 mg/ml alb) | 10% FCS (2.5 mg/ml alb) | 25 kGy 10% S/Fr II + III (2.4 mg/ml alb) | 25 kGy 20% S/Fr II + III (4.8 mg/ml alb) | 25 kGy 30% S/Fr II + III (7.1 mg/ml alb) | 25 kGy 40% S/Fr II + III (9.5 mg/ml alb) | 25 kGy 50% S/Fr II + III (11.9 mg/ml alb) |
| 0 | 77 | 104 | 100 | 65 | 71 | 82 | 84 | 82 |

S/S with no supplement;
FCS: foetal calf serum;
alb: albumin;
kGy: kilo Grays mented with 10% S/Fr-II+III, a PDT of 83.04, viability of 91.07% and 5.87×10$^6$ cells/75 cm$^2$ were obtained.

EXAMPLE 9

Subculture of the CHO Cell Line with Ham F12 Medium Supplemented by 20% Fraction II+III Supernatant (25 kGy)

The sub-culture is performed in the same way as in the previous example but using Ham F12 medium supplemented with 20% fraction II+III supernatant (25 kGy) instead of 50%.

Following various passes using the culture medium supplemented with 20% S/Fr-II+III (25 kGy), it was observed that the culture remained viable and had growth capacity.

In this case, viability, PDT and total number of cells in 75 cm$^2$ were monitored during 6 consecutive passes, average viability being 97.13%, average PDT 86.32 hours and average total number of cells 5.96×10$^6$ cells/75 cm$^2$.

EXAMPLE 10

Stability of the Fr-II+III supernatant, measured as the proliferation percentage of CHO cells, supplemented with 50% Fr-II+III supernatant reconstituted in Ham F12, compared with the medium supplemented with 10% foetal calf serum.

TABLE 1

Lyophilised stability at 4° C.

|  | T = 0 | T = 105 days | T = 112 days | T = 168 days |
|---|---|---|---|---|
| Plate 1 | 129.69 | 113.85 | 140.70 | 79.52 |
| Plate 2 | 138.75 | 84.11 | 148.71 | 87.40 |
| Average | 134.22 | 98.98 | 144.71 | 83.46 |

The Fr-II+III supernatant remains stable (proliferation percentages equal to (100±20) % or greater than FCS) for at least 168 days in lyophilised form, stored in a freezer (2° C.-8° C.).

TABLE 2

Reconstituted stability ≦ −18° C.

| Batch 1 | T = 0 | T = 98 days | T = 105 days | T = 113 days |
|---|---|---|---|---|
| Plate 1 | 129.69 | 111.36 | 136.82 | 136.53 |
| Plate 2 | 138.75 | 118.08 | 75.27 | 154.03 |
| Average | 134.22 | 114.72 | 106.05 | 145.28 |
| Batch 2 | T = 0 | T = 28 days | T = 91 days | T = 98 days |
| Plate 1 | 79.52 | 159.77 | 76.00 | 132.29 |
| Plate 2 | 87.40 | 184.16 | 171.67 | 133.30 |
| Average | 83.46 | 171.96 | 123.84 | 132.79 |

This material, reconstituted in Ham F12 culture medium, is stable for at least 113 days at a temperature of less than or equal to −18° C. (cell proliferation percentages equal to or greater than time zero).

The invention claimed is:

1. A cell culture medium for the culture of mammalian cells, comprising basal culture media for mammalian cell culture and supernatant of fraction I of human plasma fractionation or supernatant of fraction II+III of human plasma fractionation,
the supernatant of fraction 1 being prepared by
precipitation with ethanol by adding ethanol to plasma up to a concentration of approximately 8% (volume/volume) and reducing temperature to approximately −2° C.,
separation of the supernatant,
freezing or drying of the supernatant, and
subsequent addition of the resulting supernatant to the basal cell culture,
or the supernatant of fraction II+III being prepared by
precipitation with ethanol by adding ethanol to a concentration of about 20% to about 25% (volume/volume) and reducing temperature to approximately −5° C.,
separation of the supernatant,
freezing or drying,
and subsequent addition of the resulting supernatant to the basal cell culture,
wherein these supernatants have an albumin content between 60% and 78% and a gammaglobulins content between 1.5% to 12.5%.

2. The medium according to claim 1, wherein the supernatants are obtained from mixtures (pools) from at least 1000 human donors.

3. The medium according to claim 1, wherein the supernatant is dried.

4. The medium according to claim 1, wherein the supernatant is frozen.

5. A process of preparing a mammalian cell culture medium comprising obtaining a supernatant of fraction I of human plasma fractionation by
precipitation with ethanol by adding ethanol to plasma up to a concentration of approximately 8% (volume/volume) and reducing temperature to approximately −2° C.,
separation of the supernatant,
freezing or drying of the supernatant, and
subsequent addition of the resulting supernatant to the basal cell culture, or obtaining a supernatant of fraction II+III of human plasma fractionation by
precipitation with ethanol by adding ethanol to a concentration of about 20% to about 25% (volume/volume) and reducing temperature to approximately −5° C.,
separation of the supernatant,
freezing or drying, and
subsequent addition of the resulting supernatant to the basal cell culture.

6. The process of claim 5, wherein the dried supernatant is reconstituted in the basal culture medium, in distilled water or deionised and apyrogenic water, or in saline solutions or buffers commonly used in cell culture.

7. The process of claim 5, wherein the dried supernatant is reconstituted in the basal culture medium.

8. The process of claim 5, wherein the human plasma is obtained from mixtures (pools) from at least 1000 human donors.

9. A method of culturing mammalian cells comprising the steps of preparing a culture medium including supernatant of fraction I of human plasma fractionation or supernatant of fraction II+III of human plasma fractionation, the supernatant of fraction I being prepared by
precipitation with ethanol by adding ethanol to plasma up to a concentration of approximately 8% (volume/volume) and reducing temperature to approximately −2° C.,
separation of the supernatant,
freezing or drying of the supernatant, and
subsequent addition of the resulting supernatant to the basal cell culture, or the supernatant of fraction II+III being prepared by precipitation with ethanol by adding ethanol to a concentration of about 20% to about 25% (volume/volume) and reducing temperature to approximately −5° C.,
separation of the supernatant,
freezing or drying, and
subsequent addition of the resulting supernatant to the basal cell culture.

* * * * *